United States Patent [19]

Chiron et al.

[11] Patent Number: 5,606,168
[45] Date of Patent: Feb. 25, 1997

[54] IN SITU TENSILE TESTING MACHINE AND SAMPLE FOR A SCANNING ELECTRON MICROSCOPE

[75] Inventors: Rémi Chiron, Groslay; Jacques Fryet, Bobigny; Patrick Viaris De Lesegno, Saint-Leu-La-Foret, all of France

[73] Assignee: Centre National De La Recherche Scientifique, Paris Cedex, France

[21] Appl. No.: 537,694

[22] PCT Filed: Apr. 29, 1994

[86] PCT No.: PCT/FR94/00495

§ 371 Date: Dec. 8, 1995

§ 102(e) Date: Dec. 8, 1995

[87] PCT Pub. No.: WO94/25846

PCT Pub. Date: Nov. 10, 1994

[30] Foreign Application Priority Data

Apr. 30, 1993 [FR] France .................................. 93 05169

[51] Int. Cl.⁶ .................................................. G01N 23/225
[52] U.S. Cl. .................... 250/443.1; 250/442.11
[58] Field of Search ..................... 250/440.11, 442.11, 250/443.1, 310; 269/86, 55

[56] References Cited

U.S. PATENT DOCUMENTS

| | | | |
|---|---|---|---|
| 3,107,522 | 10/1963 | Bonewits | 73/103 |
| 3,919,558 | 11/1975 | Brouillette et al. | 250/443 |
| 4,548,085 | 10/1985 | Grundy | 73/862.48 |
| 4,721,000 | 1/1988 | Scanlon | 73/833 |
| 4,970,895 | 11/1990 | Houghton | 73/159 |
| 4,996,433 | 2/1991 | Jones et al. | 250/442.11 |
| 5,056,372 | 10/1991 | Estano | 73/859 |
| 5,195,379 | 3/1993 | Cussac et al. | 73/859 |
| 5,355,683 | 10/1994 | Taylor | 250/443.1 |

FOREIGN PATENT DOCUMENTS

| | | |
|---|---|---|
| 0477085 | 3/1992 | European Pat. Off. . |
| 1234255 | 10/1960 | France . |
| 2248751 | 5/1975 | France . |
| 2930805 | 2/1981 | Germany . |
| 58-218636 | 12/1983 | Japan . |
| 3-273134 | 12/1991 | Japan . |

OTHER PUBLICATIONS

Patent Abstracts of Japan, vol. 16, No. 92 (P. 1321), dated Mar. 6, 1992, corresponding to Japanese Patent Publication No. 3–273134 (Shimadzu Corp.), dated Dec. 4, 1991 (English Language).

Patent Abstract of Japanese Patent Publication No. 58–218636 (Tokyo Shibaura Denki K.K.), published on Dec. 19, 1983 (English language).

Patent Abstracts of Japan, vol. 8, No. 72 (P–265), dated Apr. 4, 1984.

Patent Abstracts of Japan, vol. 16, No. 92 (P–1321), dated Mar. 6, 1992. International Search Report and Annex.

*Primary Examiner*—Bruce C. Anderson
*Attorney, Agent, or Firm*—Greenblum & Bernstein P.L.C.

[57] ABSTRACT

The invention relates to an in situ tensile testing machine (1) and specimen designed to be placed in the observation chamber of a scanning electron microscope (S.E.M.), and to receive the specimen.

The machine is composed of a rigid frame (2) on which are disposed two traction heads (3, 4), at least one being movable, and each defining a cavity (3A, 4A) in which the corresponding end (9A, 9B) of the specimen (9) is capable of being anchored. The machine automatically locks and aligns the specimen.

This modular and compact traction testing unit can be integrated without alteration into the microscope's observation chamber. A device (22) for heating the specimen (9) can be integrated into the machine. A reversing device is used to compress the specimen.

14 Claims, 7 Drawing Sheets

IN SITU TENSILE TESTING MACHINE AND SAMPLE FOR A SCANNING ELECTRON MICROSCOPE

This application is a 371 of PCT/FR94/00495, Apr. 24, 1994, published as WO94/25846, Nov. 10, 1994.

This invention concerns an in situ tensile testing machine designed to be integrated into the observation chamber of a scanning electron microscope (S.E.M.), and to receive a specimen interposed between two anchoring elements capable of allowing the sample to be brought under traction via its ends, in order to study its behaviour.

It concerns, for example, the carrying out of observations by scanning electron microscope to follow the chronology of events at the time of plastic deformation of materials (damage, location of deformations, etc.).

This allows observation on the microscopic scale of the appearance and evolution of slip lines, shear bands, interfacial decoherences, cracks, and even deformation heterogeneities in polycrystals.

The following experiments in particular make use of in situ tensile testing at ambient temperature:

1) the study of metallic matrix composites, particularly aluminium matrix composites and those reinforced with particles of silicon carbide (SiC), with emphasis on local damage mechanisms, especially at the matrix-SiC interface level;

2) the study of materials having very high mechanical characteristics prepared by powder metallurgy, with interest more particularly focused on the detrimental effects of exogenous inclusions, introduced during preparation;

3) the study of plastic deformation instabilities in shear bands in mono-, multi- and polycrystals.

4) the study of plastic deformation heterogeneities in polycrystals, in order to characterise the plastic deformation mechanisms of polycrystalline aggregates.

At the present time, traction machines producing high forces are bulky and do not therefore allow a material to be characterised during its deformation through its analysis by scanning electron microscope. Now, in view of that mentioned above, the scientific merits of such a characterisation are very obvious, notably for the study of certain "technological" materials, to test certain behavioural models under real conditions, or even to study deformation instabilities or heterogeneities.

Moreover, in situ devices currently available on the market cannot replace conventional machines, notably because of inferior mechanical rigidity, or a less efficient sample anchoring system, or less precise checking of the mechanical displacements of the traction heads leading to generally less accurate testing.

Moreover, these devices are heavy and bulky, requiring modifications of the access door to the chamber of the S.E.M., or may only be partly modular, with the specimen traction motor placed outside the chamber so as to avoid the effects of magnetic interference of the electronic beam, or they may not allow a sufficient nominal load to be imposed.

Furthermore, it is important to mention that the systems generally adopted to anchor the sample comprise either self-locking jaws, which are unable to guarantee automatic alignment or the absence of sliding of the sample in the heads, or the broaching of the sample in a clevis. Neither of these two systems allows the sample to be thermally insulated; tests at high temperature are therefore only possible on samples with a long useful length and small cross-section, in order to minimise heat conduction away from the heated useful zone towards the anchoring heads of the sample.

These anchoring systems therefore present a major drawback for traction tests on solid samples at high temperatures, because of the excessive thermal conduction towards the fixing heads and frame of the machine; substantial heating power would be required to attain high temperatures (>600° C.); in addition, during testing over a long period of time, the process would result in considerable heating of the fixing heads and the rest of the machine, which may in time cause irreversible deterioration of the machine's characteristics.

Thus, patent JP-A-03273134 describes a material testing machine comprising a scanning electron microscope. A sample is gripped between a clamp contiguous to a fixed part of the device and a loading clamp. These clamps or jaws hold the sample by pinching.

Moreover, patent EP-A-0.477.085 describes a device for testing a sample under traction and compression after simulating re-entry into the atmosphere. A sample subjected to the testing is produced from a pad in which two half-moon-shaped slots are made, and which bear upon two shoulders in the form of arcs of a circle placed at the base of a chuck presenting a ribbed bearing plate.

The fact of conducting high-temperature tests on a solid sample is of definite scientific interest in many lines of research in field of mechanics and physical metallurgy, and in particular:

the study of plasticity of metal aggregates and monocrystals at medium and high temperature, with the purpose of characterising intra and intergranular deformation mechanisms as a function of temperature;

the study of plasticity of "technological" materials used at medium or high temperature, such as superalloy monocrystals in the precipitated phase $Ni/Ni_3 Al$ studied at 650° C. which is the service temperature of the base of aircraft jet turbine blades.

The object of the present invention is to overcome the different drawbacks mentioned above by proposing a traction machine that partially combines the advantages of conventional machines but does not present the drawbacks of other in situ testing machines (bulk, and/or absence of modularity, poor rigidity, inefficient sample anchoring system), and at the same time allows the sample to be heated without affecting the machine.

A reversing device associated with the machine of the invention also allows it to be used, in a preferred embodiment, as an in situ compression machine.

To achieve this, the invention comprises an in situ tensile testing machine designed to be placed in the observation chamber of a scanning electron microscope (S.E.M.) and receive a specimen interposed between two anchoring elements capable of allowing traction in one direction of said specimen by its ends, with a view to studying its behaviour.

It is composed of a rigid frame on which two traction heads are arranged, of which at least one is movable, and each of which defines a cavity in which the corresponding end of the specimen is capable of being anchored by means of two shoulders forming a narrowing opposing the sliding of the end of the specimen in the direction of traction in order to automatically lock it, in such a way as to form a modular, compact traction assembly, capable of being integrated without alteration into the observation chamber of a S.E.M.

This modular, compact aspect of the machine also allows it to be adapted to other characterisation systems (optical microscope, X-diffraction machine, etc.).

The present invention also concerns the following characteristics, taken alone or in any feasible combination thereof.

The ends of the specimen bear respectively upon the shoulders of a corresponding traction head, by means of two slugs forming rollers, mounted freely between each said shoulder and a corresponding side part facing the end of the specimen, in such a way as to simultaneously ensure automatic locking and automatic aligning of said specimen.

Advantageously, the slugs are made up of cylinders of semi-circular section, the diametrical plane of which symmetrically bears upon each of the respective shoulders of said traction heads, the semi-circular parts of said slugs co-operating with side parts having cylindrical bearing surfaces of semi-circular section of radius identical to that of the slugs, produced on either side of each end of the specimen.

In this case, each of the shoulders of each traction head is inclined towards the longitudinal axis of a specimen in place, in such a way as to automatically lock said specimen by a wedging effect and simultaneously and automatically align it.

The shoulders of each traction head form a 45° angle with the longitudinal traction axis.

According to another particularly useful embodiment of the invention, during high-temperature testing, the slugs freely interposed between the traction heads and the ends of the specimen present compressive strength properties and thermal insulation for the specimen itself.

To achieve this, the material making up the slugs is therefore a ceramic. Preferably, the ceramic is a zirconium oxide ZrO2 stabilised with magnesium MgO allowing a field of application in the temperature range 0° to 800° C.

According to a further embodiment of the invention, a constant traction speed is obtained by a direct current motor, slaved in speed thanks to a tachometric unit and an electronic speed slaving system, and by means of a speed reducer whose output force is transmitted to the movable traction head by a screw-nut system.

The motor is integrated into the module which it composes, and comprises magnetic shielding.

Furthermore, force and displacement sensors are used during a test to obtain a record of force as a function of deformation.

The step-down ratio of the speed reducer is 3000 to 1.

According to a further embodiment of the invention, the machine comprises means allowing it to be used with an inclination adjustable from 0° to 70°, at the minimum working distance of 30 mm. At 70° maximum inclination, it then becomes possible, during deformation, to determine locally both the deformation field obtained by a microextensometer technique, and the crystalline field of rotation of the specimen obtained by the analysis of the neighbouring crystallographic texture, by diffraction of back-scattered electrons (E.B.S.P. system).

According to another embodiment of the invention, the machine is fixed onto a standard plate of the scanning electron microscope (S.E.M.) allowing the X, Y, Z displacements to be used, independent in three orthogonal directions.

Its nominal loading capacity is 10 kN, with an admissible overload of up to 15 kN.

In addition, it is interfaced with a computer.

According to another embodiment of the invention, the machine allows hot traction testing of the specimen by means of a heating device integrated into the module which it composes.

In this case, the heating device is made up of an oven attached by pins below the specimen and in close contact with it in a median part, said specimen being thermally insulated in relation to the traction heads and to the machine in general, thanks to intermediate ceramic slugs, against which said specimen bears in the traction heads.

According to a further embodiment of the invention, a first temperature measuring and regulation thermocouple is placed between the oven and the specimen, and a second thermocouple is used to measure the temperature of the traction heads.

To allow the machine of the invention to be used as an in situ compression machine, it can be fitted with a reversing device which receives the traction applied by the machine and applies compression to a specimen.

This reversing device comprises two compression jaws each anchored in one of the traction heads and having an L-shaped finger, facing one another, between which the specimen can be placed.

The invention will be better understood and other features of it highlighted by the following description, in reference to the attached schematic drawings, illustrating, for the purposes of non-limiting examples, how the invention can be produced.

Figure 1:
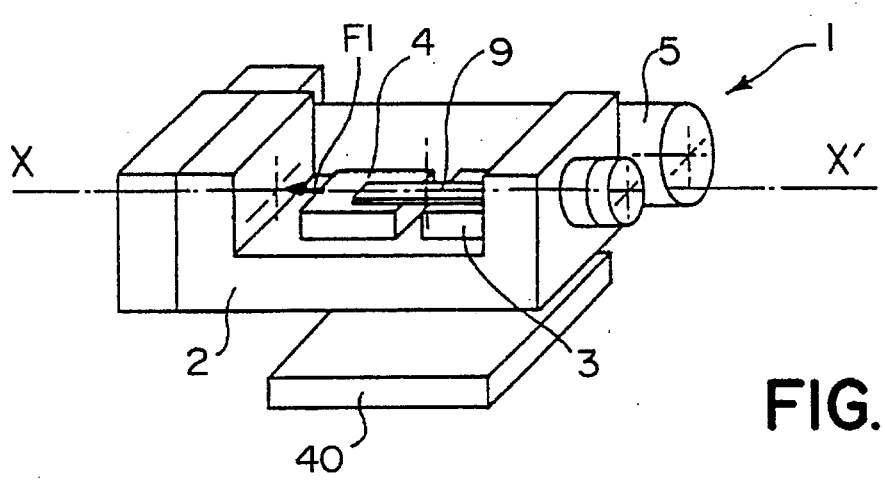
FIG. 1 shows diagrammatically in perspective a traction machine according to the invention.

The traction machine 1, designated in its entirety and represented diagrammatically in FIG. 1, is made up of a U-shaped rigid frame 2, on which two traction heads 3 and 4 are arranged, of which one 4 is movable along an axis XX'.

A constant traction speed is obtained by a direct current motor 5, slaved in speed thanks to a tachometric unit 6, designated in its entirety, and by means of two speed reducers 7 and 8, interposed between said tachometric unit 6 and the motor 5. The output force resulting from the speed reducer is transmitted to the movable traction head by a screw-nut system 30.

The traction heads 3 and 4 define cavities, respectively 3A and 4A, in which ends 9A, 9B of specimen 9 are able to anchor.

This anchoring is effected by means of two shoulders 10 and 11 for the cavity 4A, and 12 and 13 for the cavity 3A, forming respectively narrowings 14 and 15 opposing the sliding of ends 9A, 9B of the sample 9 in a direction of traction F1, and ensuring its automatic locking.

Machine 1, thus globally composed, is designed to be integrated into the observation chamber of the scanning electronic microscope (S.E.M.) without modifying it in any way, the chamber therefore retaining its original configuration and dimensions.

For this same reason of complete integration, the motor 5 comprises a magnetic shielding 18.

The specimen is machined from a plate having parallel faces. It comprises a thin central zone, called the useful zone, between two wider ends designed to be anchored to the traction heads.

More precisely, the ends 9A, 9B of the specimen 9, or of the compression device, bear respectively on the shoulders 10, 11 and 12, 13 of a corresponding traction head 4 or 3, by means of two slugs 16 forming rollers, mounted freely between each said shoulder and a corresponding side part facing the end 9A, 9B of specimen 9, in such a way as to simultaneously ensure automatic aligning and automatic locking of said specimen.

Figure 12:
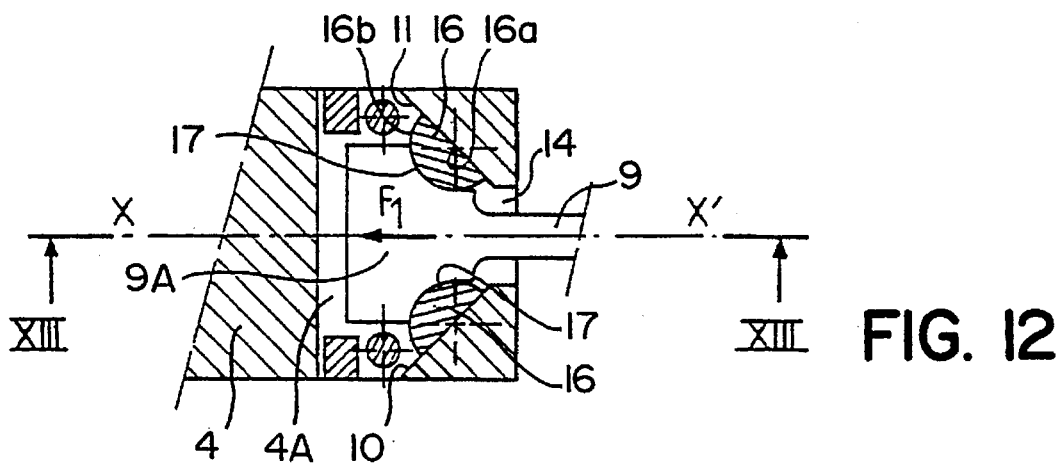
FIG. 12 shows a detailed view of a traction head of the machine, in which one end of a specimen to be tested is inserted.
Figure 13:
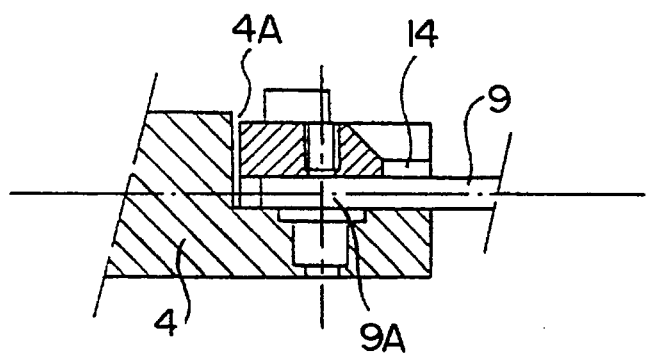
FIG. 13 shows a cross-sectional view along line XIII—XIII of FIG. 12.
Figure 14:
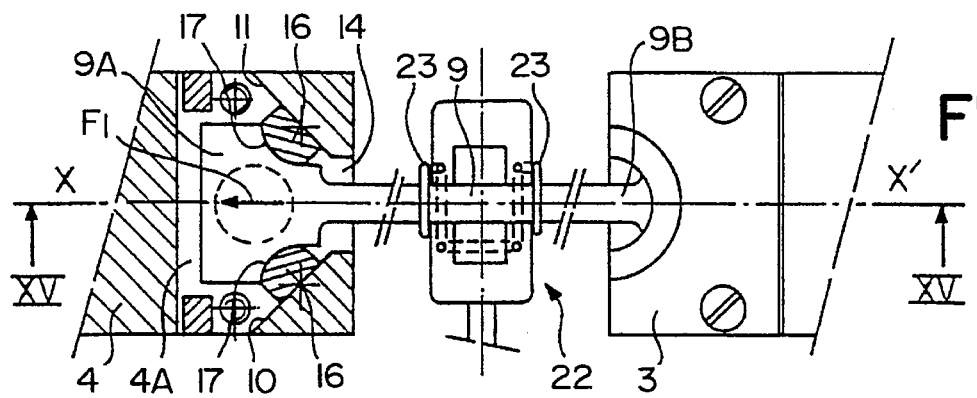
FIGS. 14 and 15 are, respectively, a plan view of a traction machine fitted with a device for heating the specimen, and a sectional side view along line XV—XV of FIG. 14.

According to the embodiment shown in FIGS. 12 or 14, the slugs 16 are made up of half-cylinders, the diametrical plane 16a of which bears symmetrically on each of the respective shoulders 10, 11 and 12, 13 of the traction heads 4, 3, the semi-circular parts 16b of said slugs 16 co-operating with side parts 17 having a cylindrical bearing surface and a radius identical to that of slugs 16, said side parts 17 being produced either side of each end 9A, 9B of specimen 9.

Each shoulder 10, 11, and 12, 13 of each traction head 4, 3 is inclined towards the longitudinal axis XX' of a specimen 9 in position, in such a way as to ensure automatic locking of said specimen by a wedging effect achieved simultaneously with its automatic alignment.

Preferably, shoulders 10, 11 and 12, 13 of each traction head 4, 3, form a 45° angle with longitudinal axis XX'.

The four slugs 16 interposed freely between the traction heads 4, 3 and the ends 9A, 9B of the specimen 9, or of the compression device, present characteristics of compressive strength and thermal insulation for specimen 9 itself, or for the compression device.

To achieve this, the constituent material of slugs 16 is a ceramic, made up of a zirconium oxide ZrO2 stabilised with magnesium MgO, allowing a field of application in the temperature range 0° to 800° C., permitting hot testing, as will be described more amply herein below.

The machine also comprises force and displacement sensors which allow recording of force as a function of deformation during a test. The displacement sensor (20) is also protected by magnetic shielding 21 in mu-metal, etc.

According to a concrete embodiment of the machine, the following characteristics are obtained for tests at ambient temperature:

- Ratio of speed-reducer: 3000 to 1
- Nominal force: 10 kN
- Maximum force: 15 kN
- Displacement speed: 0.01 to 30 μm/s
- Distance of travel: 1=21 mm
- Sensors: force and displacement
- Weight: 2 kg

- Overall dimensions: 15.5×9.5×4.5 cm$^3$.

Before the first prototype was brought into service in the laboratory, two certification tests were conducted at the maximum load of 15 kN. In order to meet requirements relating to weight, which must be as low as possible, and also the strength of the machine, conventional strength calculations of the materials were carried out during the design stage, notably tensile and bending strength calculations, which made it possible to carefully dimension and select materials (at nominal force, the safety factor retained is in the order of 5). The frame 2 is therefore in soloralu, a high mechanical strength aluminium alloy (AZ5GU, tensile strength=540 MPa), and the anchoring heads 4, 3 of the specimen 9 and the moving parts (gears, traction screw) are in treated copper-beryllium (Cu-Be) (tensile strength=1200 MPa).

Figure 2:
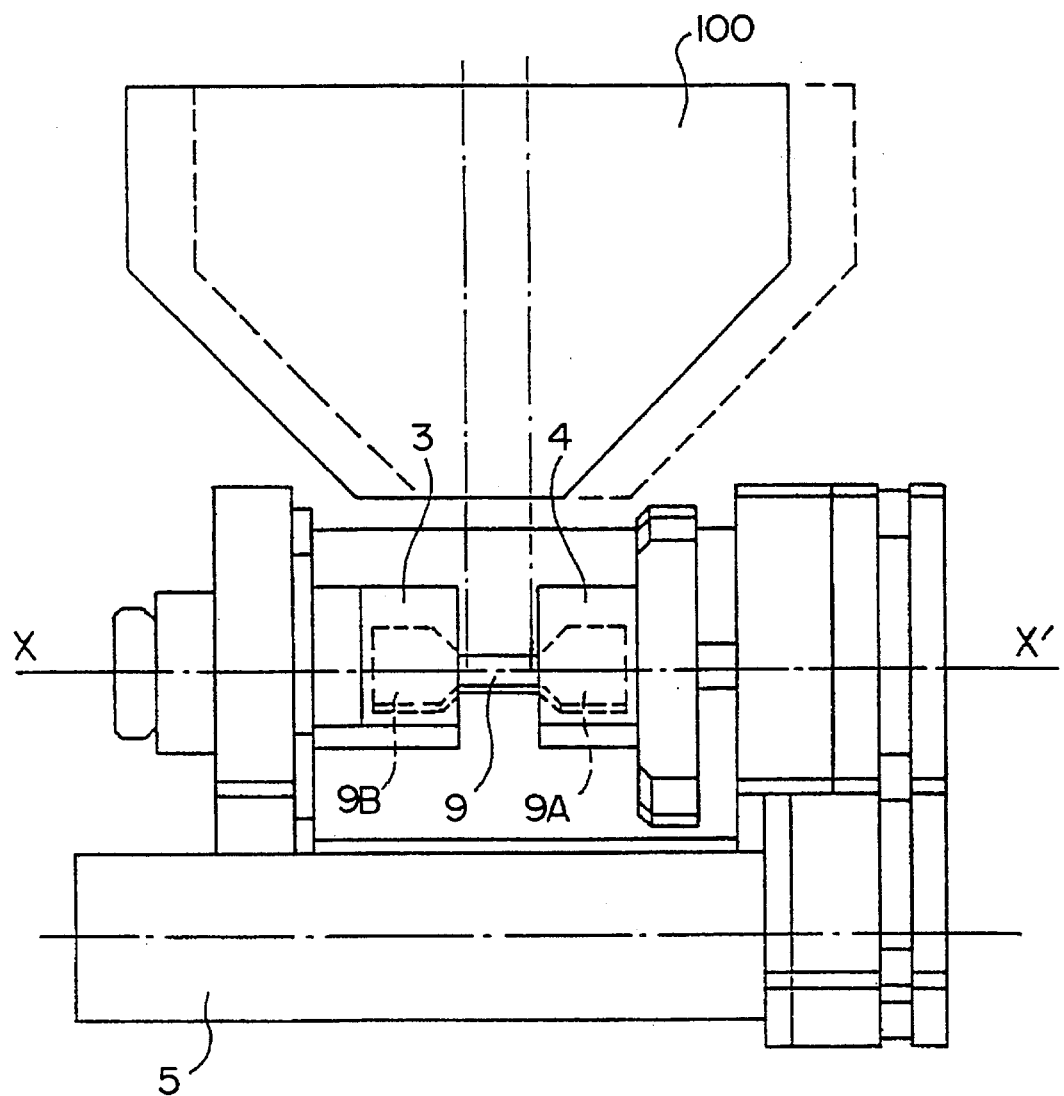
FIGS. 2, 3 and 4 show, respectively, a front view, side view and above view, of a machine according to FIG. 1, in the maximum inclination position on a scanning electron microscope (S.E.M.)
Figures 3, 4:
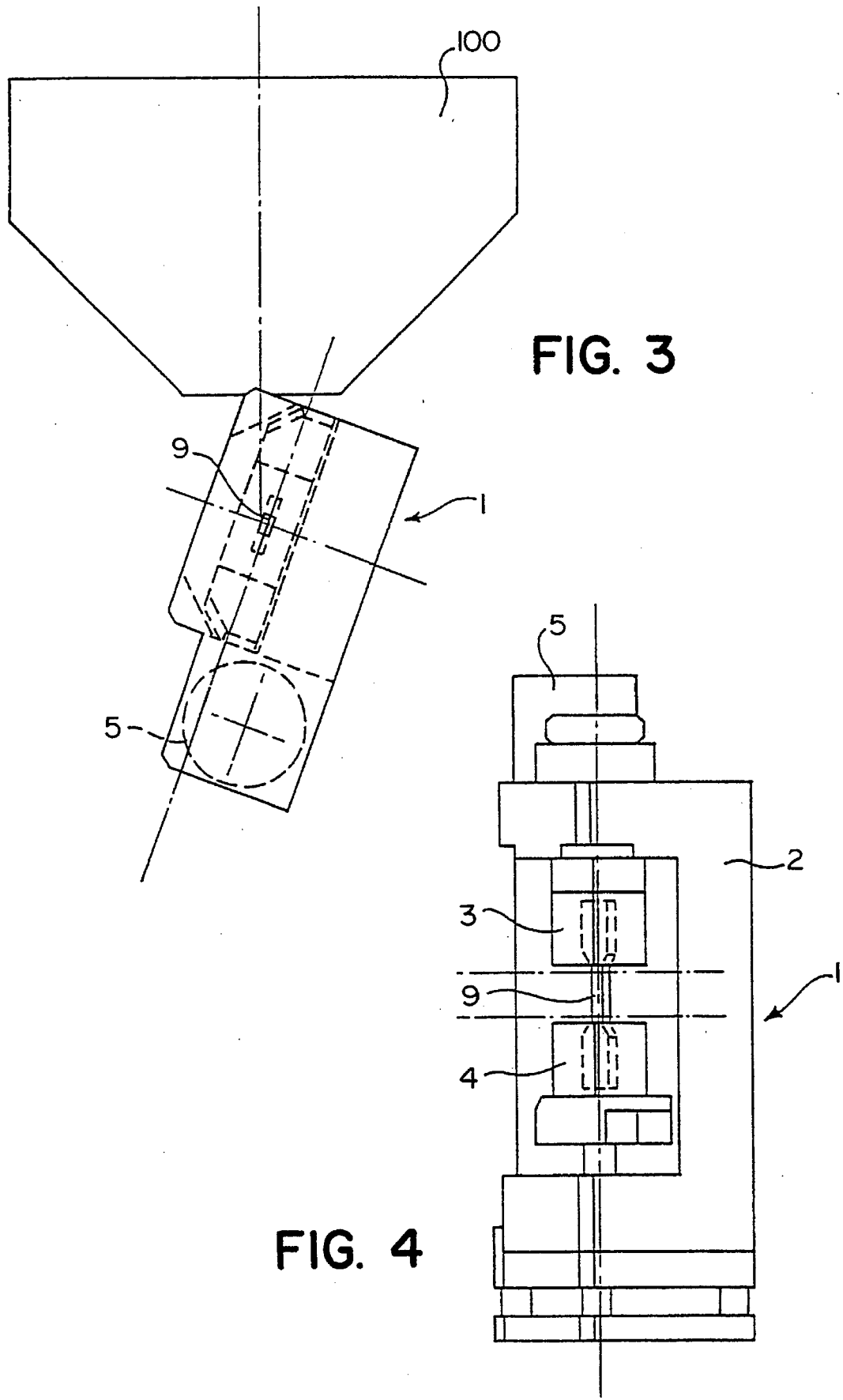
Figure 5:
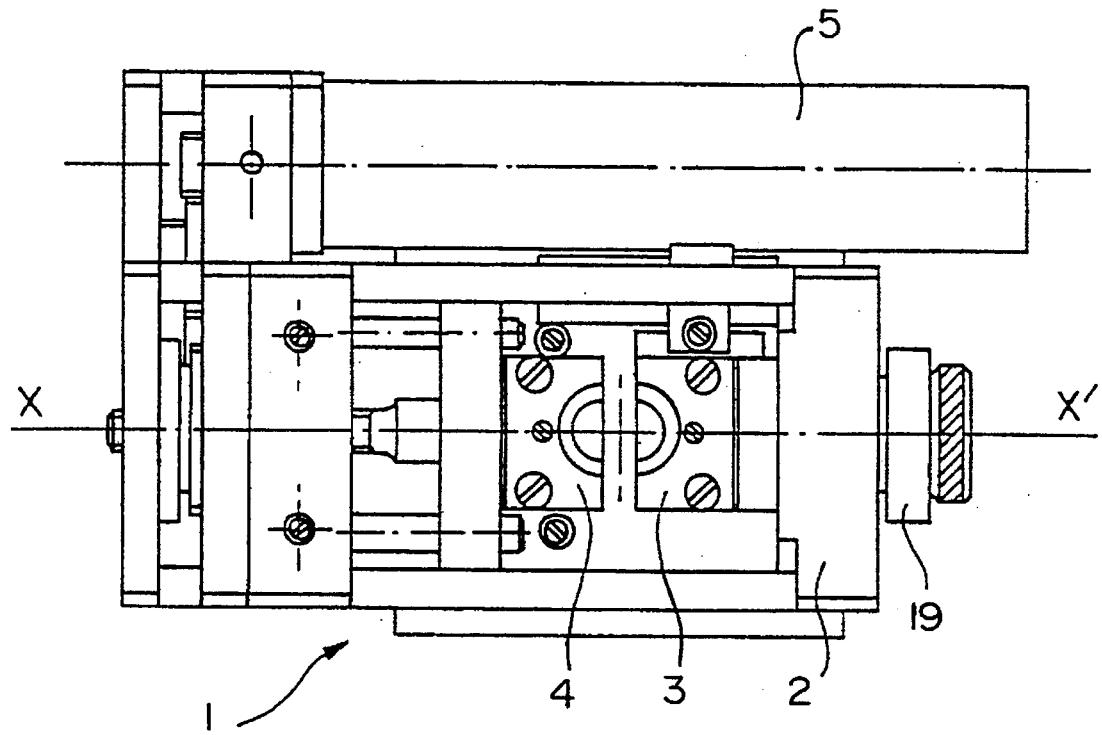
FIG. 5 shows a plan view of a traction machine according to one of the preceding figures.
Figure 6:
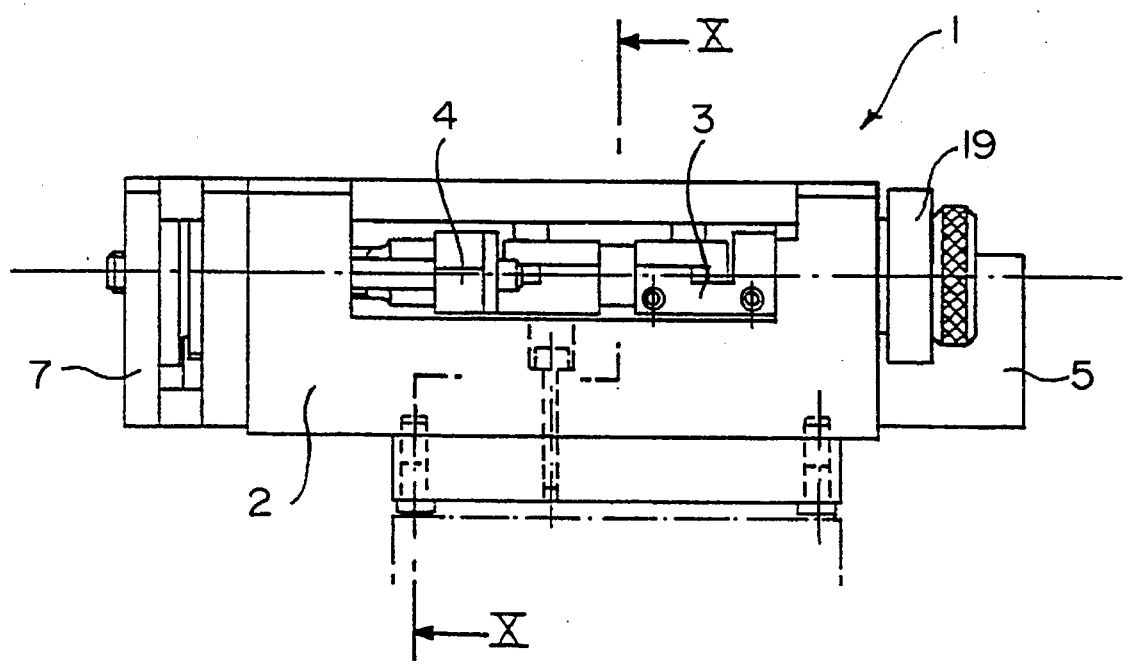
FIG. 6 shows a side view according to FIG. 5.
Figure 7:
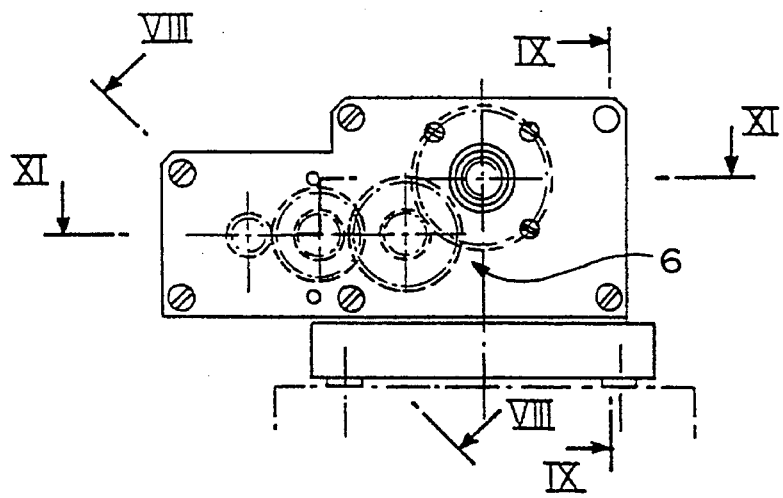
FIG. 7 shows an end view according to FIG. 6.
Figure 8:
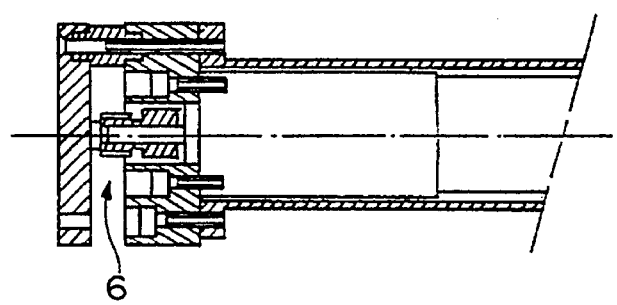
FIG. 8 shows a cross-sectional view along line VIII—VIII of FIG. 7.

Another embodiment of the machine according to the invention is that it comprises means allowing it to be used with a inclination variable from 0° to 70°, at the minimum working distance of 30 mm, making it possible, during deformation, to determine locally both the deformation field and the field of rotation of the specimen 9, to analyze the neighbouring crystallographic texture by diffraction of backscattered electrons (E.B.S.P. system) (See FIGS. 2, 3 and 4).

The machine can therefore be fixed onto the scanning stage of the S.E.M., allowing the X, Y and Z displacements to be used, independently in three orthogonal directions.

Figure 9:
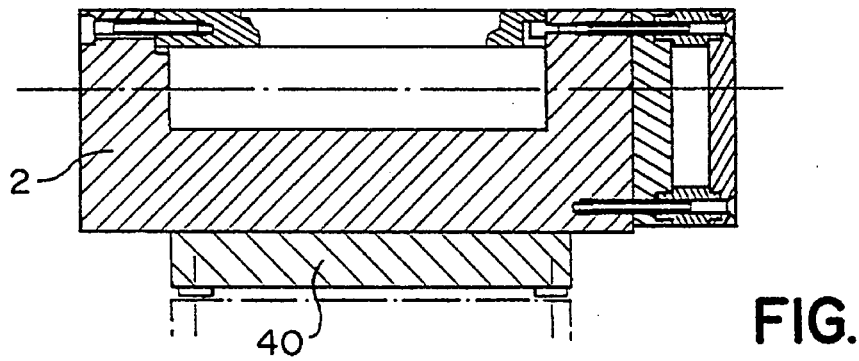
FIG. 9 shows a cross-sectional view along line IX—IX of FIG. 7.
Figure 10:
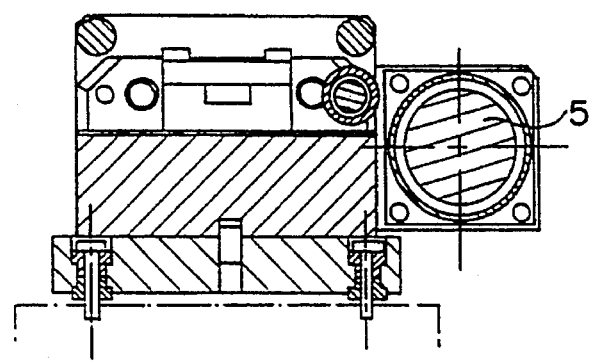
FIG. 10 shows a cross-sectional view along line X—X of FIG. 6.
Figure 11:
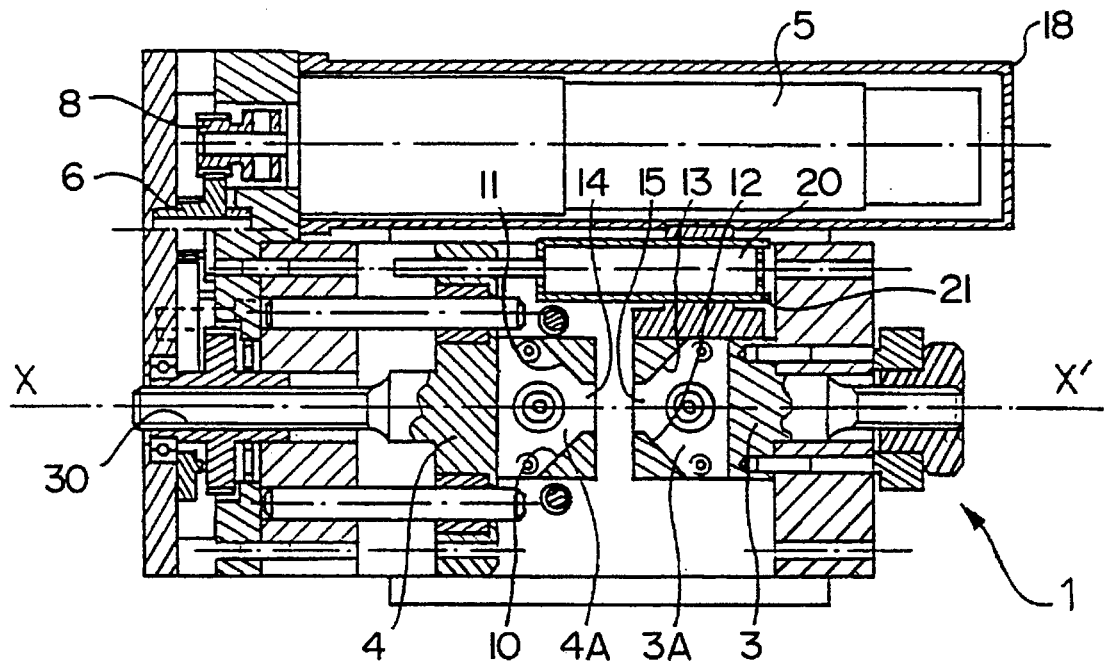
FIG. 11 shows a cross-sectional view along line XI—XI of FIG. 7.

This fixing is effected by means of the plate 40 (FIG. 9).

In addition, the machine is interfaced with a computer. Acquisition and computer processing of the data (force and displacement) make it possible in particular to produce traction cycles slaved to the stress or deformation experienced by the specimen, in addition to normal use at the prescribed deformation speed.

Figure 15:
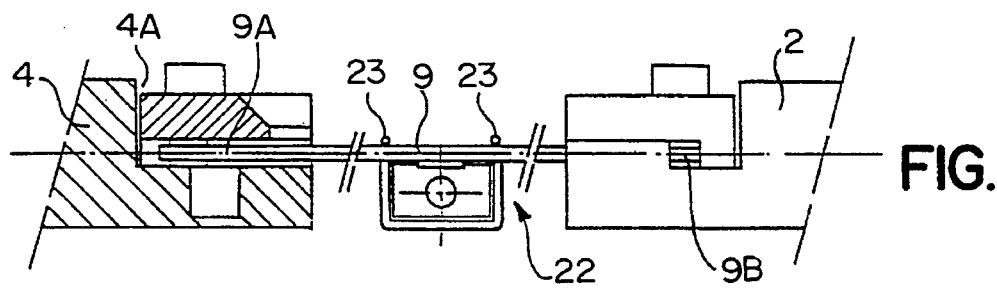

According to a modified embodiment, (FIGS. 14 and 15) a heating device 22, designated in its entirety, is integrated into the module formed by the traction machine.

This device 22 is made up of an oven attached by pins 23 below specimen 9 and in close contact with it in a median part, said specimen 9 being thermally insulated from the traction heads 4, 3, and in turn from the machine in general, thanks to the intermediate ceramic slugs 16 on which said specimen 9 bears in the traction heads 4, 3.

The technical characteristics of the oven 22 are as follows:

- Nominal temperature: 800° C.
- Nominal power: 50 W
- Temperature measurement: by thermocouple
- Temperature regulation: by PID regulator When the heating device is used, the characteristics of the machine are limited as follows:

- Nominal force: 5 kN
- Maximum force: 10 kN
- Distance of travel: 1=10 mm.

The heating oven 22, attached by pins 23 below specimen 9, is in close contact with said specimen.

A first temperature measuring (and regulation) thermocouple is placed between the oven and the specimen, and a second thermocouple is used to measure the temperature of the anchoring heads of specimen 9.

For long duration tests conducted at high temperature, it is necessary to cool the entire machine (in a vacuum, and considering the dimensional characteristics of the specimen and oven, heat dissipates mainly by conduction), to avoid excessive heating, particularly at the level of the anchoring heads of specimen 9, and of force and displacement sensors 19 and 20 respectively.

Figure 16:
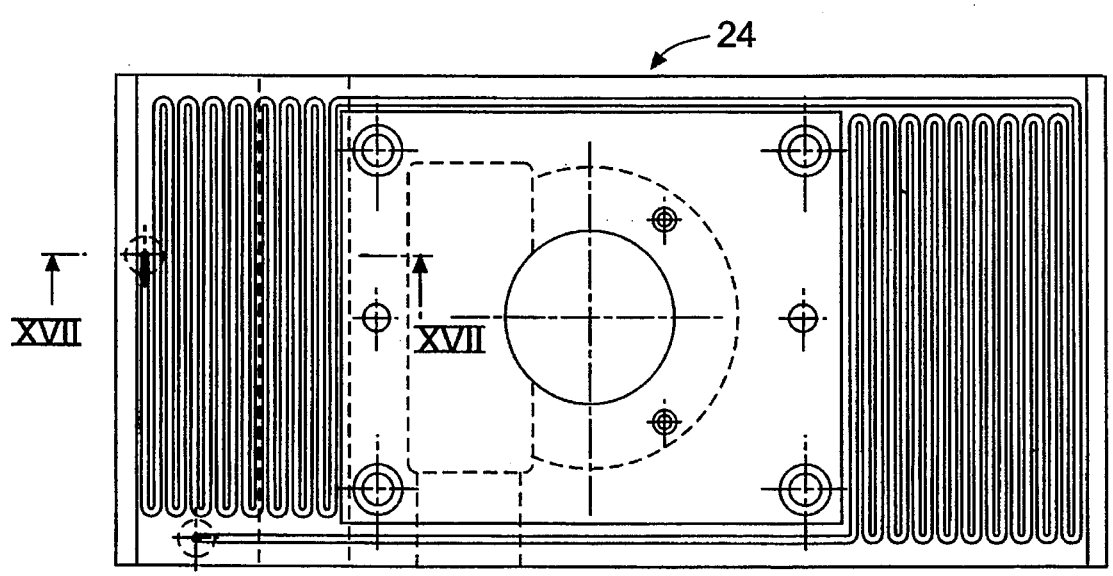
FIG. 16 is a plan view of the main element of a heat exchanger of the heating device.
Figure 17:
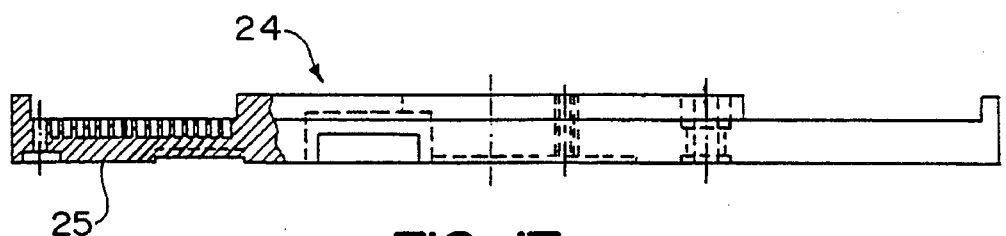
FIG. 17 is a sectional side view along line XVII—XVII of FIG. 16.
Figure 18:
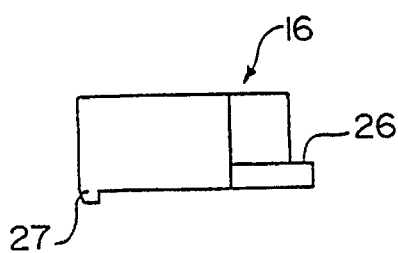
FIGS. 18, 19 and 20 are side, top and bottom enlarged-scale views of a ceramic ZrO2/MgO slug according to one embodiment.
Figure 21:
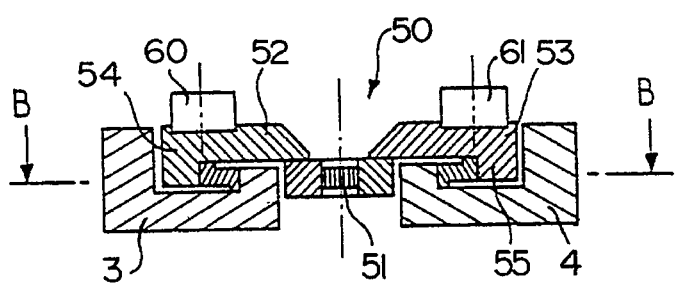
FIGS. 21 to 23 are representations of the traction head fitted with the reversing device for compression testing, respectively cross-sectional view AA, an above view and a cross-sectional view BB.
Figure 19:
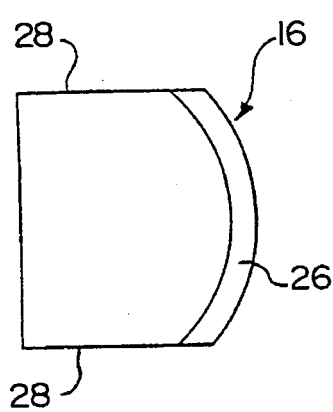
Figure 22:
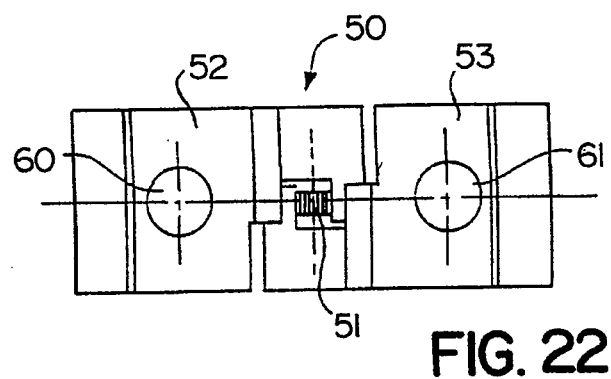
Figure 20:
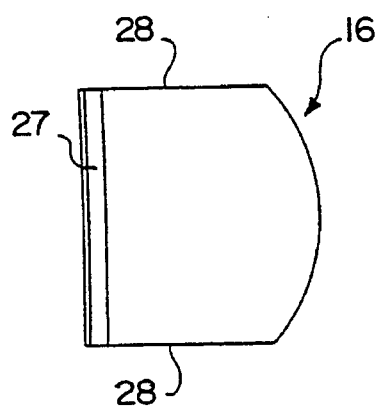
Figure 23:
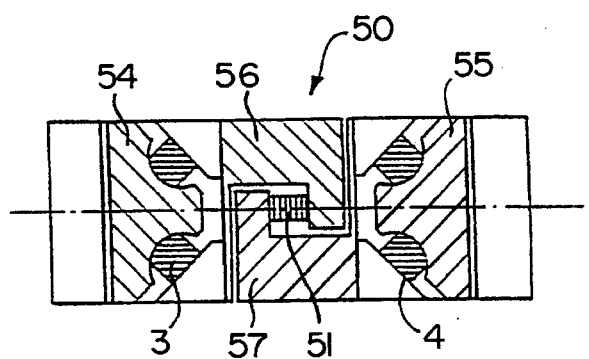
Figure 24:
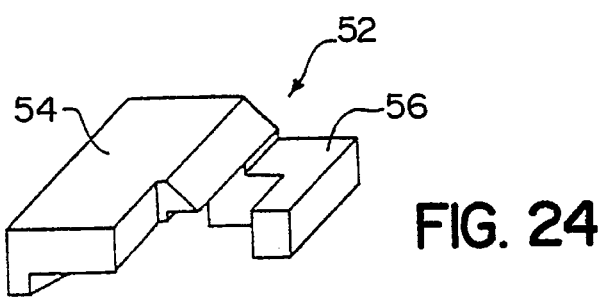
FIG. 24 is a view in perspective of one of the compression jaws.

FIGS. 16 and 17 represent the main element of a cooling system 24 making up heat sink 25 used to evacuate calories: it is designed in such a way that the temperature of the anchoring heads of the specimen 9 does not exceed 50° C., by using air flowing at a high rate as a heat exchanging fluid.

In order to conduct in situ traction tests at high temperature, it is necessary to thermally insulate specimen 9 from the rest of the machine. For this, the original anchoring system already described is used (four half-slugs bearing on 45° inclined planes), but the nature and form of the four half-slugs are modified so as to thermally insulate specimen 9 in relation to anchoring heads 4, 3.

The studs are made from zirconium oxide ZrO2 type ceramic doped in magnesium MgO; this material presents the best characteristics of both compressive strength (it must resist the compression resulting from the loading of the specimen) and thermal insulation in the range 0° to 800° C.

The maximum operating temperature (800° C.) of the device results from a trade-off between the needs of the users and the influence of the temperature of the specimen on the correct working of the microscope (notably the detectors), due to the increase in radiation as the temperature increases.

As already mentioned, the four ZrO2/MgO semi-slugs have a dual role:

they permit the load to be applied to specimen 9: at the maximum temperature of 800° C. their compressive strength must be in the order of 500 MPa (it is given to be greater than 1800 MPa at 20° C.);

they thermally insulate specimen 9 from the rest of the machine in a geometrically simple and efficient way (at 800° C., the thermal conductivity k of $ZrO_2/MgO$ is less than 2 $Wm^{-1}k^{-1}$): the specimen must not touch the metal anchoring heads 4, 3 during the test and it must be possible to place the specimen in position with the same ease as for conventional tests at ambient temperature.

To attain this double objective, the lower portion of slugs 16 has a semi-peripheral shoulder 26 which prevents specimen 9 in place against said slugs 16 from coming into thermal contact with the bottom of cavities 4A or 3A of heads 4 or 3.

Another feature of slugs 16 resides in the fact that they only bear against the bottom of cavities 4A or 3A via a heel 27. Thus, not only is the thermal contact with the traction heads limited solely to the heel, but also any possible pivoting of slugs 16 about this heel along F2 during traction assists their automatic alignment.

The cylindrical part of the ceramic slugs 16 is reduced in favour of two parallel side wings 28 defining thus a smaller section of the base, in order to reduce thermal conduction towards the anchoring heads of the specimen.

The traction machine of the invention has been described so far in relation to its primary use for the application of traction to specimen 9. However, by equipping this machine with a reversing device 50, it can be used to apply compression forces to a specimen 51.

It is thus possible to study a specimen subjected to compression forces under the electron microscope with all the advantages mentioned hereinabove: application of substantial forces, compatibility of the machine with the volume of the chamber of the S.E.M., etc.

The reversing device 50 includes two compression jaws 52, 53 each comprising a base 54, 55 similar in form to that of the ends of the traction specimen 9 described herein above and designed to co-operate with the traction heads 3 and 4.

Each of these bases 54, 55 is integral with an L-shaped finger 56, 57.

These fingers are opposite each other and nested in each other, as shown in FIGS. 24 to 27, in such a way as to allow specimen 51 to be interposed between them.

Thus, the traction force applied to the bases 54 and 55 of the compression jaws 52, 53 of the reversing device 50 produces compression forces applied to specimen 51.

Without substantial modification, the machine of the invention therefore also allows study of the effects of compression forces under an electronic microscope.

Ovens 60 and 61 can be fixed onto compression jaws 52, 53.

The energy which they supply heats specimen 51 essentially by conduction. It is therefore possible to study compression forces at a chosen, possibly high, temperature.

The reference signs inserted after the technical characteristics mentioned in the claims serve only to facilitate the understanding of said claims and in no way limit their scope.

We claim:

1. An in situ tensile testing machine for placement in an observation chamber of a scanning electron microscope and for receipt of a specimen interposed between two anchoring elements capable of allowing traction in one direction of the specimen by the ends thereof, for studying behavior of the specimen, said machine comprising:

a rigid frame;

two traction heads disposed on said rigid frame, at least one of said traction heads being movable and each said traction head defining a cavity for anchoring a respective end of the specimen by means of a pair of shoulders forming a narrowing opposing a sliding end of the specimen in a traction direction;

each said end of the specimen bearing upon said shoulders of a respective one of said traction heads by means of two slugs forming rollers, mounted freely between each said shoulder and a corresponding side part facing an end of the specimen.

2. A machine according to claim 1, wherein:

said slugs are comprised of cylinders of semi-circular section, a diametrical plane of which symmetrically bears upon each of the respective shoulders of said traction heads, semi-circular parts of said slugs cooperating with said parts having cylindrical bearing surfaces of semi-circular section of radius identical to that of the slugs, produces on either side of each end of the specimen.

3. A machine according to claim 2, wherein:

each of the shoulders of each said traction head being inclined with respect to a longitudinal traction axis.

4. A machine according to claim 2, wherein:

the shoulders of each said tractionhead form a 45° angle with a longitudinal traction axis.

5. A machine according to claim 1, wherein:

the four slugs, interposed freely between the traction heads and the ends of the specimen, have excellent properties of compressive strength and thermal insulation for the specimen.

6. A machine according to claim 5, wherein:

the constituent material of the slugs is a ceramic.

7. A machine according to claim 6, wherein:

the ceramic is a zirconium oxide ZrO2 stabilized with magnesium MgO.

8. A machine according to claim 1, wherein:

a constant traction speed is obtained by a direct current motor, slaved in speed due to a tachometric unit and an electric speed slaving system, and by means of a speed reducer having an output force transmitted to the movable traction head by a screw-nut system.

9. A machine according to claim 8, further comprising:

force sensors and displacement sensors for providing a means of obtaining, during a test, a recording of force (F) as a function of deformation (l).

10. A machine according to claim 1, wherein:

said machine is adapted to be fixed onto a standard stage of the scanning electron microscope allowing the X, Y, and Z displacements to be used, independent in three orthogonal directions.

11. A machine according to claim 1, wherein:

said machine comprises an integrated heating device.

12. A machine according to claim 11, wherein:

said heating device comprises an oven attached by pins below the specimen and in close contact with the specimen in a median part.

13. A machine according to claim 12, wherein:

a first temperature measuring and regulation thermocouple is positioned between the oven and the specimen and a second thermocouple is used to measure the temperature of said traction heads.

14. A machine according to claim 1, wherein:

said machine comprises a reversing device for receiving traction applied by the machine and for applying compression to a specimen, the device comprising two compression jaws each anchored in one of said traction heads and each having an L-shaped finger, facing one another, between which a specimen can be placed.

* * * * *